(12) United States Patent
Lim et al.

(10) Patent No.: US 11,052,263 B2
(45) Date of Patent: Jul. 6, 2021

(54) BODY INSERTABLE DEVICE HAVING ADJUSTABLE RADIATION EMISSION DIRECTION

(71) Applicants: NATIONAL CANCER CENTER, Goyang-si (KR); KOREA INSTITUTE OF RADIOLOGICAL & MEDICAL SCIENCES, Nowon-gu (KR); THE ASAN FOUNDATION, Songpa-gu (KR); UNIVERSITY OF ULSAN FOUNDATION FOR INDUSTRY COOPERATION, Nam-gu (KR)

(72) Inventors: Young Kyung Lim, Paju-si (KR); Jung Won Kwak, Namyangju-si (KR); Dae Yong Kim, Goyang-si (KR); Yeon Joo Kim, Goyang-si (KR); Joo Young Kim, Goyang-si (KR); Soon Ki Min, Goyang-si (KR); Young Dae Jung, Seoul (KR); Ho Jin Jeong, Jinju-si (KR); Sang Hyoun Choi, Seoul (KR); Ui Jung Hwang, Goyang-si (KR)

(73) Assignees: NATIONAL CANCER CENTER, Goyang-Si (KR); KOREA INSTITUTE OF RADIOLOGICAL & MEDICAL SCIENCES, Seoul (KR); THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 268 days.

(21) Appl. No.: 16/312,788

(22) PCT Filed: Jun. 19, 2017

(86) PCT No.: PCT/KR2017/006381
§ 371 (c)(1),
(2) Date: Dec. 21, 2018

(87) PCT Pub. No.: WO2018/004166
PCT Pub. Date: Jan. 4, 2018

(65) Prior Publication Data
US 2019/0329066 A1  Oct. 31, 2019

(30) Foreign Application Priority Data

Jul. 1, 2016  (KR) .................... 10-2016-0083434

(51) Int. Cl.
*A61N 5/10* (2006.01)
(52) U.S. Cl.
CPC ......... *A61N 5/1016* (2013.01); *A61N 5/1007* (2013.01); *A61N 5/1014* (2013.01);
(Continued)
(58) Field of Classification Search
CPC .......... A61N 5/1016; A61N 2005/1094; A61N 2005/1008; A61N 5/1014;
(Continued)

(56) References Cited

U.S. PATENT DOCUMENTS 3,060,924 A  10/1962 Rush
8,808,156 B1  8/2014 Godfrey, Jr. et al.
(Continued)

FOREIGN PATENT DOCUMENTS

CN  102100947 A  6/2011
CN  204734852 U  11/2015
(Continued)

OTHER PUBLICATIONS

Japanese Office Action for Application No. 2018-569020, dated Dec. 2, 2019, 2 pages.
(Continued)

*Primary Examiner* — Kaylee R Wilson
(74) *Attorney, Agent, or Firm* — McCarter & English, LLP (57) ABSTRACT

The present invention relates to a body insertable device having an outer body being bent; and an inner body positioned inside the outer body, having an accommodation space in which the resource soured is accommodated, and
(Continued)

being capable of rotating inside the outer body, wherein a radiation emission direction is continuously adjusted by rotation of the inner body.

14 Claims, 11 Drawing Sheets

(52) U.S. Cl.
CPC ............... *A61N 2005/1005* (2013.01); *A61N 2005/1008* (2013.01); *A61N 2005/1094* (2013.01)

(58) Field of Classification Search
CPC .......... A61N 2005/1005; A61N 5/1007; A61N 2005/1018
See application file for complete search history.

(56) References Cited

U.S. PATENT DOCUMENTS

| | | | | |
|---|---|---|---|---|
| 8,979,725 | B2 * | 3/2015 | D'Andrea | A61N 5/1016 600/6 |
| 2003/0149327 | A1 | 8/2003 | Chin et al. | |
| 2005/0277802 | A1 | 12/2005 | Larsen et al. | |
| 2008/0009658 | A1 | 1/2008 | Smith et al. | |
| 2009/0209805 | A1 | 8/2009 | Lubock et al. | |
| 2011/0215260 | A1 | 9/2011 | Kleinwaechter et al. | |
| 2011/0224478 | A1 | 9/2011 | Hannoun-Levi et al. | |
| 2014/0288350 | A1 * | 9/2014 | Kleinwaechter | A61N 5/1014 600/7 |

FOREIGN PATENT DOCUMENTS

| | | |
|---|---|---|
| EP | 2239005 A1 | 10/2010 |
| JP | 2001-190700 A | 7/2001 |
| JP | 2009-540924 A | 11/2009 |
| JP | 4602356 B2 | 12/2010 |
| JP | 2012-502781 A | 2/2012 |
| KR | 20-0394440 Y1 | 9/2005 |
| KR | 10-2009-0074145 A | 7/2009 |
| WO | 2007/149363 A2 | 12/2007 |
| WO | 2014/021947 A1 | 2/2014 |

OTHER PUBLICATIONS

International Search Report for PCT/KR2017/006381 dated Sep. 14, 2017, pp. 1-3.
Chinese Office Action for Application No. 201780040257.1, dated Feb. 25, 2020, 5 pages.
European Office Action for Application No. 17820443.4, dated Feb. 6, 2020, 5 pages.

* cited by examiner

BODY INSERTABLE DEVICE HAVING ADJUSTABLE RADIATION EMISSION DIRECTION

CROSS-REFERENCE TO RELATED APPLICATIONS

The present application is a U.S. national stage application, filed under 35 U.S.C. § 371(c), of International Application No. PCT/KR2017/006381, filed on Jun. 19, 2017, which claims the priority of Korean Application No. 10-2016-0083434, filed on Jul. 1, 2016. The entire contents of the aforementioned applications are incorporated herein by reference.

TECHNICAL FIELD

The present invention relates to an insertable device and, more particularly, to a body insertable device for brachytherapy.

BACKGROUND ART

Radiation therapy for cancer patients may be classified largely into two types: external beam radiation therapy where radiation is delivered to a tumor from a radiation source placed outside a patient's body, and brachytherapy where radiation is delivered from a radiation source placed inside a patient's body.

Among them, the brachytherapy is carried out by inserting the radiation source into a tumor and delivering a high radiation dose to the tumor, and there is an advantage that the radiation dose transmitted to surrounding healthy organs may be reduced significantly.

In the brachytherapy, radiation is emitted by moving the radiation source through an insertable device inserted into a human body, but there is a problem that a technology for adjusting three-dimensional radiation intensity using the insertable device by adjusting a radiation direction has not been developed enough.

In particular, when a bent insertable device needs to be used to emit radiation to a tumor which is located like uterine cancer, it is difficult to assign an intensity adjusting function to the insertable device.

DISCLOSURE

Technical Problem

An object of the present invention is to provide an insertable device for brachytherapy, the device which is bent and capable of adjusting radiation intensity.

Technical Solution

The above objects of the present invention can be achieved by an insertable device including: an outer body including a first outer body extending in a long manner, a second outer body extending in a long manner, and a bent part for connecting the first outer body and the second outer body such that the first outer body and the second outer body are bent; a first inner body positioned inside the first outer body, and having an accommodation space in which a radiation source is accommodated; a second inner body positioned inside the second outer body, having a guide space enabling the radiation source to pass therethrough, and being capable of operating the rotation thereof; and an inner connection part positioned in correspondence to the bent part inside the outer body, having a connection space communicating with a guide space and the accommodation space such that the radiation source is allowed to pass therethrough, and connecting the first inner body and the second inner body, wherein the first inner body is separated from the first outer body and rotated by the rotation of the second inner body.

The accommodation space may be formed to extending in a long manner along the first inner body.

The accommodation space may be formed in a trench form within the first inner body.

The insertable device may further include a position limiting part positioned close to the first outer body within the accommodation space and limiting a position of the radiation resource.

A vertical cross section of the first inner body in a lengthwise direction may be in a circular shape, and the accommodation space may accommodate the radiation source at an eccentric position.

The inner connection part may include a rotation power mechanism.

The rotation power mechanism may include at least one of a flexible shaft, a bellows, or a joint.

One end of the inner connection part may be fixed to the first inner body, and the other end of the inner connection part may be connected to the second inner body.

The inner connection part and the outer body may be spaced from each other, such that the inner connection part rotates in correspondence to the outer body when the inner connection part is transformed in response to rotation of the second inner part.

The accommodation space may include: a first accommodation space; and a second accommodation space positioned between the first accommodation space and the connection space, and the second accommodation space may have a cross-sectional area greater than a cross-sectional area of the first accommodation space.

The cross-sectional area of the second accommodation space may increase in proportion to proximity to the connection space.

The guide space may include: a first guide space; and a second guide space positioned between the first guide space and the connection space, and the second guide space may have a cross-sectional area greater than a cross-sectional area of the first guide space.

The cross-sectional area of the second guide space may increase in proportion to proximity to the connection space.

The first inner body may be made of a material with excellent radiation shielding performance, compared to the first outer body.

An angle of emission of radiation from the radiation source to an outside of the first outer body may be 5 degrees to 180 degrees.

The above objects of the present invention can be achieved by an insertable device including: an outer body being bent; and an inner body positioned inside the outer body, having an accommodation space in which the resource soured is accommodated, and being capable of rotating inside the outer body, wherein a radiation emission direction is continuously adjusted by rotation of the inner body.

The inner body may include: a first inner body in which the accommodation space is formed; a second inner body having an operator capable of operating rotation; and a flexible shaft connecting the first inner body and the second inner body and being bent.

Advantageous Effects

According to the present invention, there is provided an insertable device for brachytherapy, which is bent and capable of adjusting radiation intensity.

MODE FOR INVENTION

Hereinafter, the present invention will be described in detail with reference to the accompanying drawings.

The accompanying drawings are only examples shown in order to describe the technical spirit of the present invention in more detail. Therefore, the technical spirit of the present invention is not limited to shapes of the accompanying drawings.

An insertable device according to an embodiment of the present invention is described with reference to FIGS. 1 to 5.

Figure 1:
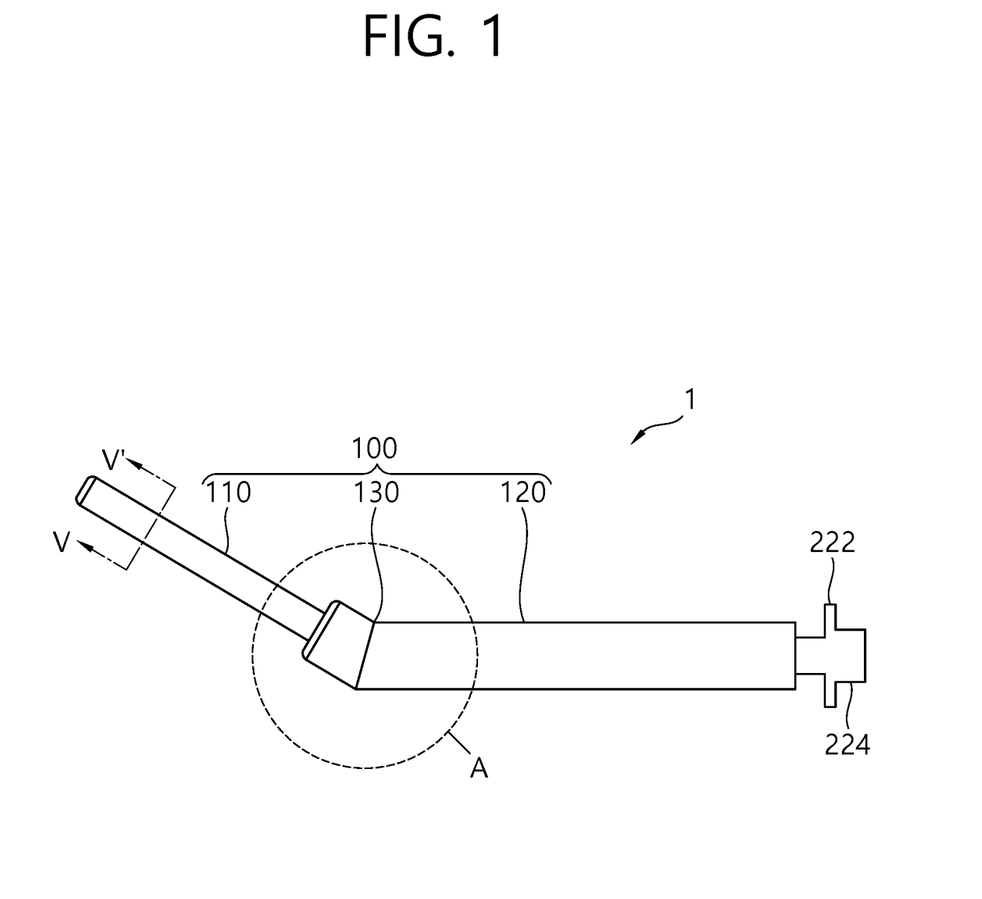
FIG. 1 is a perspective view of an insertable device according to an embodiment of the present invention.
Figure 2:
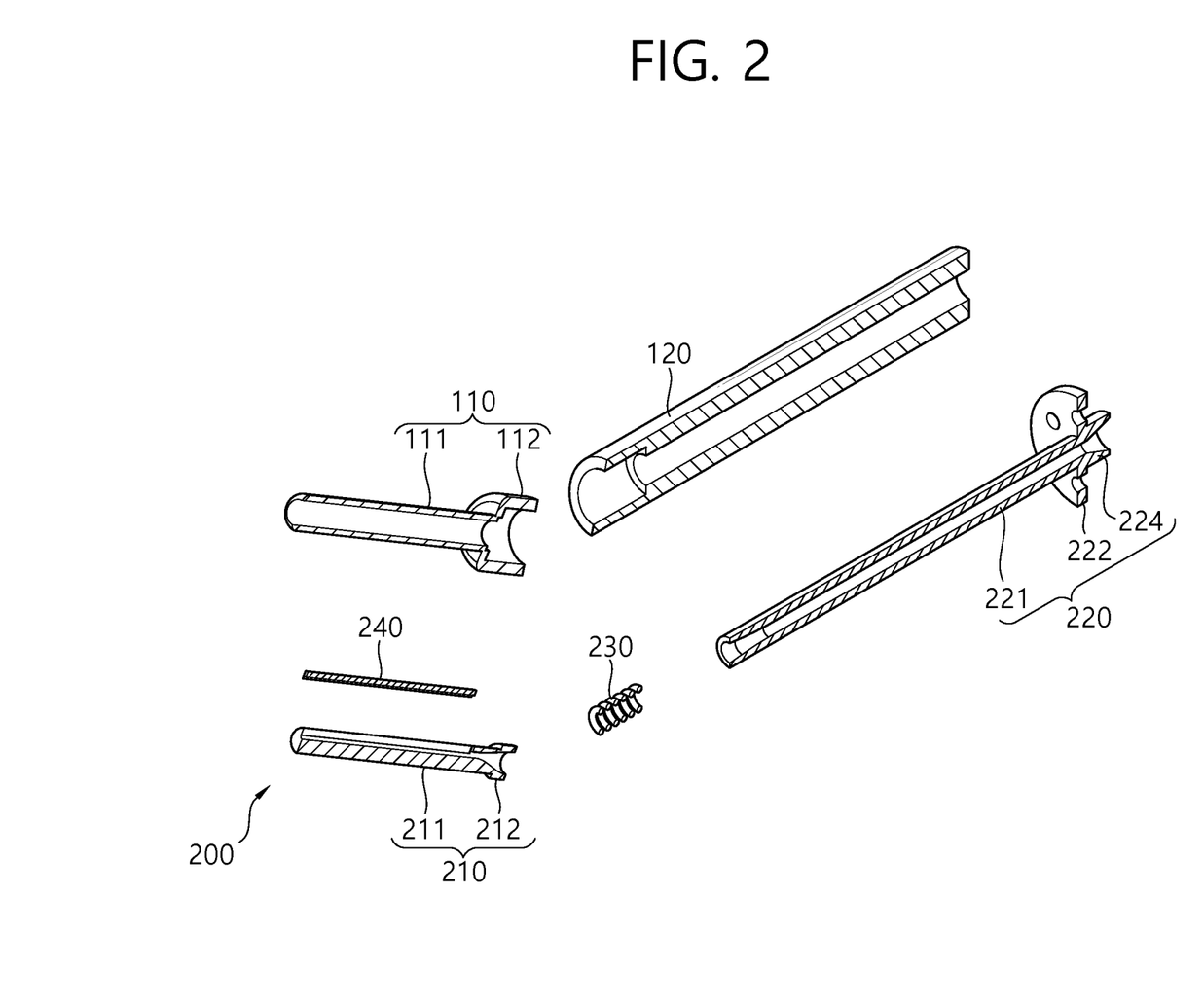
FIG. 2 is an exploded perspective view of an insertable device according to an embodiment of the present invention.
Figure 3:
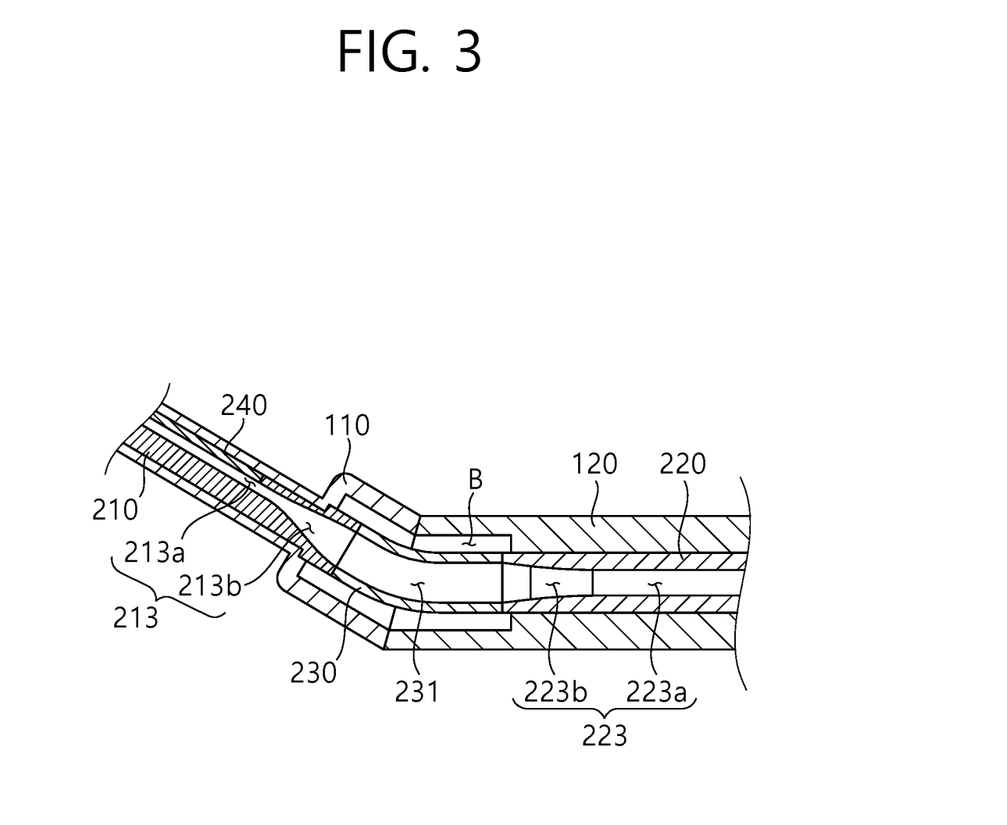
FIG. 3 illustrates inner configurations of a portion A of FIG. 1.
Figure 4A:
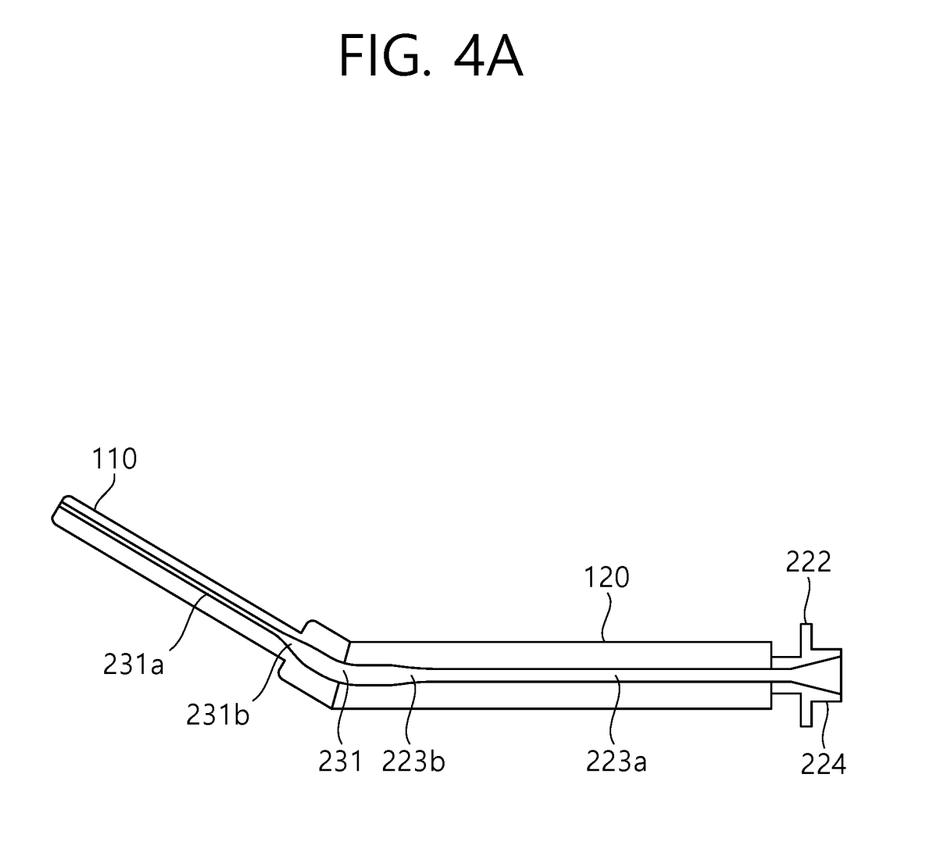
FIGS. 4A and 4B illustrate a change in a position of an accommodation space in which a radiation source is accommodated in an insertable device according to an embodiment of the present invention
Figure 4B:
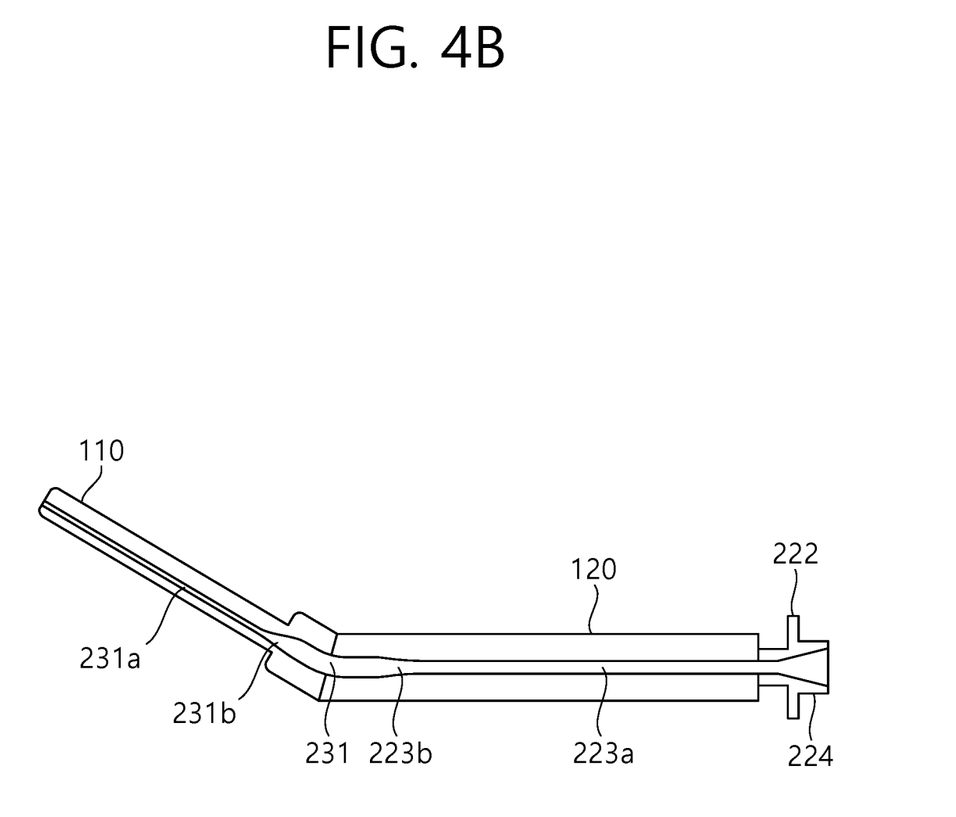
Figure 5:
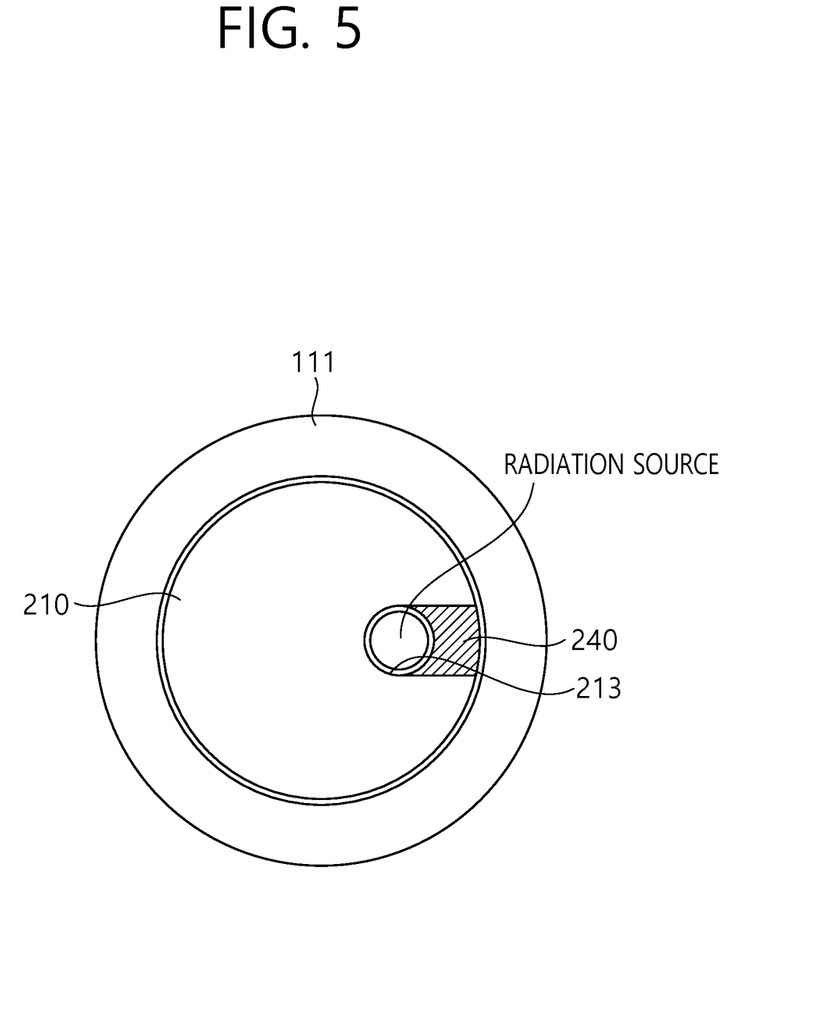
FIG. 5 illustrates a cross-sectional view taken along line V-V' of FIG. 1.
Figure 6:
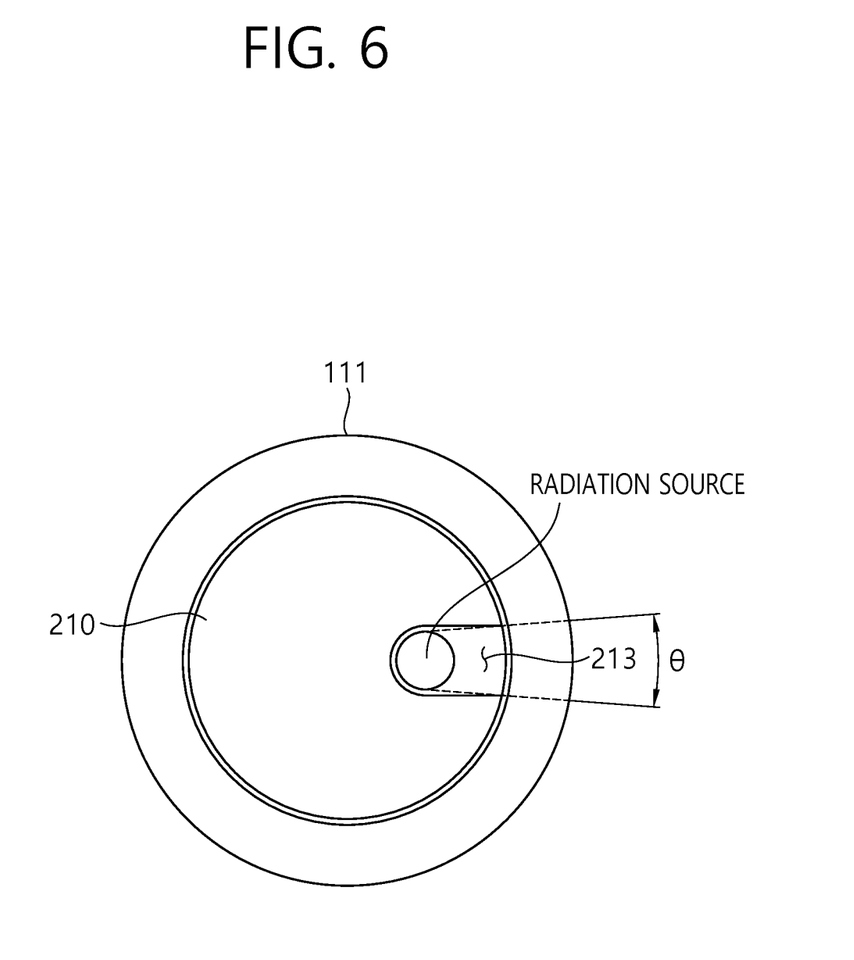
FIGS. 6 and 7 illustrate adjustment of a radiation direction in an insertable device according to the present invention.

FIG. 1 is a perspective view of an insertable device according to an embodiment of the present invention, FIG. 2 is an exploded perspective view of an insertable device according to an embodiment of the present invention, FIG. 3 illustrates inner configurations of a portion A of FIG. 1, FIGS. 4A and 4B illustrate a change in a position of an accommodation space in which a radiation source is accommodated in an insertable device according to an embodiment of the present invention, FIG. 5 illustrates a cross-sectional view taken along line V-V' of FIG. 1. FIG. 2 illustrates a perspective view of a cross section in a lengthwise direction.

An insertable device 1 according to an embodiment of the present invention is largely comprised of an outer body 100 and an inner body 200.

The outer body 100 defines an overall outer appearance of the insertable device 1, and accommodates the inner body 200 in an empty space therein. In this embodiment, an operator 222 in the inner body 200 is exposed to an outside of the outer body 100.

The outer body 100 is in an overall thin and long shape and bent. Specifically, the outer body 100 includes a first outer body 110, a second outer body 120, and a bent part 130, and the first outer body 110 and the second body 120 are connected by the bent part 130 such that the first outer body and the second outer body are bent.

Such an outer body 100 may be provided in various manners. The outer body 100 may be provided as an overall integrated body or may be provided as the first outer body 110 and the second outer body 120 are manufactured individually and coupled thereto by welding or the like. In addition, the outer body 100 may be in a form which is made such that the first outer body 110 and/or the second outer body 120 are manufactured as a plurality of parts and coupled to each other.

Each of the first outer body 110 and the second outer body 120 may have a vertical cross section in a lengthwise direction, which is in a circular shape, and a cross section of an inner space of each of the first outer body 110 and the second outer body 120 is also in a circular shape. According to an orientation of the lengthwise direction, a cross-sectional area of each of the first outer body 110 and the second outer body 120, and a cross-sectional area of the inner space of each of the first outer body 110 and the second outer body 120 change. Overall, a cross-sectional area of the second outer body 120 is greater than a cross-sectional area of the first outer body 110. In another embodiment, a cross section of the first outer body 110 and/or the second outer body 120 may be in an elliptical shape rather than the circular shape.

The first outer body 110 of the outer body 100 is primarily brought into contact or close to a treatment target (tumor or the like), and, while the first outer body 110 is brought into contact or close to the treatment target, radiation is emitted toward the treatment target from a radiation source placed inside the inner body 200. The first outer body 110 may be made of a metallic material with a low atomic number such as titanium or a non-metallic material such as plastic.

Part of the second outer body 120 is inserted into a human body, and the other part is exposed to an outside. The second outer body 120 may be made of a metallic material such as stainless steel or a non-metallic material such as plastic.

The inner body 200 includes a first inner body 210, a second inner body 220, an inner connection part 230, and a position limiting part 240.

The first inner body 210 includes a first part 211 extending in a long manner, and a second part 212 extending in width.

An accommodation space 213 extending in a long manner along a lengthwise direction is formed in the first inner body 210. The accommodation space 213 includes a first accommodation space 213a formed in the first part 211, and a second accommodation space 213b formed in the second part 212.

The first accommodation space 213a is formed in a trench form, and the second accommodation space 213b has a cross-sectional area expanded than a cross section of the first accommodation space 213a. Specifically, the second accommodation space 213b has a funnel shape, of which a cross-sectional area increases in proportion to proximity to the inner connection part 230.

The second inner body 220 is comprised of a first part 221 extending in a long manner, and a second part (an operator 222) extending in width. The operator 222 is exposed to an outside of an end of the outer body 100.

A guide space 223 extending in a long manner along a lengthwise direction is formed in the second inner body 220. The guide space 223 includes a first guide space 223a and a second guide space 223b, and the second guide space 223b is formed at a portion adjacent to the inner connection part 230 and has a cross-sectional area greater than a cross-sectional area of the first guide space 223a. Specifically, the second guide space 223b has a funnel shape, of which a cross-sectional area increases in proportion to proximity to the inner connection part 230.

Meanwhile, a third part 224 is provided on an outside of the second part 222. The third part 224 serves to connect an external radiation source to the guide space 223.

The inner connection part 230 is provided at a portion corresponding to a bent part 130 of the outer body 100, and has a connection space 231 therein. One end of the inner connection part 230 is coupled to the first inner body 210, and the other part of the inner connection part 230 is coupled to the second inner body 220 and bent in correspondence to the bent part 130. Connection of the inner connection part 230 and the inner body 210 and 220 may be performed by welding or brazing.

The inner connection part 230 is, but not limited to, a rotation power transmitting mechanism between two shafts that intersect each other and may be at least one of a flexible shaft, a bellows, or a joint. In particular, the inner connection part 230 may be a pipe-shaped flexible shaft and may be especially made of a high-carbon steel wire. In the present invention, the inner connection part 230 may have various shapes as long as the inner connection part 230 maintains an accommodation space therein and transmits rotating motion of the second inner body 220 to the first inner body 210 while corresponding to a shape of the outer body 100.

The position limiting part 240 is in a thin and long shape, and positioned at the periphery of the first accommodation space 213a. A radiation source is positioned in an empty space under the position limiting part 240 of the first accommodation space 213a (that is, a portion close to the center of the first inner body 210). That is, with the radiation source being inserted, the first outer body 110, the position limiting part 240, and the radiation source are arranged in order.

The second part (the operator 222) is exposed to an outside, and a user rotates the operator 222 to change an emission direction and adjust radiation intensity.

Insertion of the radiation source in the above-described insertable device 1 will be described.

The radiation source is connected to an end of a thin and long wire, which is provided close to an external brachytherapy device, and emits radiation.

The radiation source passes through the guide space 223 formed within the second inner body 220 and through the connection space 231 formed within the inner connection part 230, and is then finally positioned within the accommodation space 213 formed in the first inner body 210. A position of the radiation source in a lengthwise direction in the accommodation space 213 may be adjusted in various ways.

In a path of insertion of the radiation source, both ends of the connection space 231 with a diameter greater than a diameter of the first guide space 223a and a diameter of the first accommodation space 213a are connected to each other by the funnel-shaped second guide space 223b and the funnel-shaped second accommodation space 213b. Due to this structure, the guide space 223, the connection space 231, and the accommodation space 213 form a continuous structure without a step formed therein, so that the radiation resource is prevented from being stopped by the inner body 200 when being inserted, and the insertion of the radiation source is stably guided.

In addition, the radiation source is prevented from being stopped by the inner body 200 during the process of recovering the radiation source, and removal of the radiation source may be stably guided.

In another embodiment, an additional guide pipe may be used for stable insertion and recovery of the radiation source. In this case, the guide pipe may be provided over the entire length of the inner body 200 or may be provided only in the connection space 231.

Hereinafter, adjustment of radiation intensity in response to adjustment of an emission direction of the inserted radiation source is described.

In FIG. 4A, the radiation source is inserted in an upward direction. In this state, if the operator 222 is rotated in the outside, the second inner body 220 is rotated with the outer body 100 being fixed. If the second inner body 220 is rotated, the inner connection part 230 connected thereto is transformed and thus rotated. In this case, an empty space B is formed between the inner connection part 230 and the outer body 100, as shown in FIG. 3, and thus, interference with the outer body 100 does not happen despite transformation of the inner connection part 230.

Meanwhile, in another embodiment, an inner connection part 300 is in contact with the outer body 100 or brought into contact with the outer body 100 when being rotated. In this case, the inner connector 300 may be rotated while being transformed in correspondence to an inner shape of the outer body 100.

If the inner connector part 230 is rotated, the first inner body 210 connected thereto is also rotated, and thus, the position of the accommodation space for the radiation source is changed to face a downward direction, as shown in FIG. 4B. In response to the change in the position of the radiation source, a radiation emission direction is changed.

Overall, the radiation emission direction is changed in response to rotation of the operator 222, and a degree of change in the radiation emission direction may be 10% to 100%, 30% to 100%, 50% to 100%, and 80% to 100% of a degree of rotation of the operator 222. In response to the rotation of the operator 222, the radiation emission direction may be rotated by the same angle of the rotation of the operator 222.

Configurations of the operator 222 may be changed in various ways. An additional device may be further included to reduce a degree of change in the radiation emission direction in response to a different degree of rotation. In another embodiment, the operator 222 may not be integrally formed with the second inner body 220, or may rotate the second inner body 220 through an additional configuration connected to the second inner body 220 without having the operator 222 in the second inner body 220. In yet another embodiment, the second inner body 220 may be rotated through an additional mechanical-electric device.

The emission direction of the radiation source is changed in the above process, and this will be described in more detail with reference to FIG. 5.

FIG. 5 illustrates the case where the radiation source is in the accommodation space 213 of the first inner body 210. The accommodation space 213 is in a trench shape and faces the first outer body 110.

The position limiting part 240 is positioned in an upper space of the accommodation space 213, that is, a space directly facing the first outer body 110. The position of the radiation source is limited to the inside of the accommodation space 213 by the position limiting part 240. Thus, the radiation source is positioned at a predetermined distance from an outer surface (a circumferential surface) of the first inner body 210, and the distance to the outer surface is maintained constantly by the position limiting part 240.

In this arrangement, the radiation source is not positioned at the center of the first inner body 210 but is positioned eccentrically from the center thereof. The first inner body 210 is made of a material with excellent radiation shielding performance compared to the first outer body 110, and, for example, the first inner body 210 may be made of tungsten or tungsten alloy. Since the first inner body 210 has a very small diameter, it is hard to completely shield radiation in an undesired direction. According to this embodiment, the radiation source is positioned eccentrically, and thus, the first inner body 210 in a direction (a direction C in FIG. 5) in which emission of radiation from the radiation source is not desired may have a relatively great thickness. Thus, it is possible to minimize emission of radiation in an undesired direction.

The position limiting part 240 may be made of a polymer material, and, for smooth rotation of the first inner body 210, the first inner body 210 and the first outer body 110 may be spaced apart from each other and a lubricating film may be formed therebetween.

Using the insertable device according to the present invention, the brachytherapy may be performed effectively, and this is described with reference to FIGS. 6 to 9.

First, it is possible to effectively limit a radiation emission angle according to the present invention. Radiation is evenly emitted in a direction of 360 degrees from the radiation source. According to the present invention, as illustrated in FIG. 5, the radiation source is spaced from the circumferential surface of the first inner body 210. Thus, an emission angle (Θ in FIG. 6) of emission of radiation from the radiation source is limited by the first inner body 210. The emission angle is determined depending on a distance between the radiation resource and the circumferential surface of the first inner body 210, a size of the accommodation space 213, and a shape of the accommodation space 213. The radiation emission angle may be 5 degrees to 180 degrees, 5 degrees to 120 degrees, 5 degrees to 60 degrees, 5 degrees to 30 degrees, 10 degrees to 120 degrees, 10 degrees to 60 degrees, 10 degrees to 30 degrees, 30 degrees to 120 degrees, 30 degrees to 90 degrees, or 30 degrees to 60 degrees.

Figure 7:
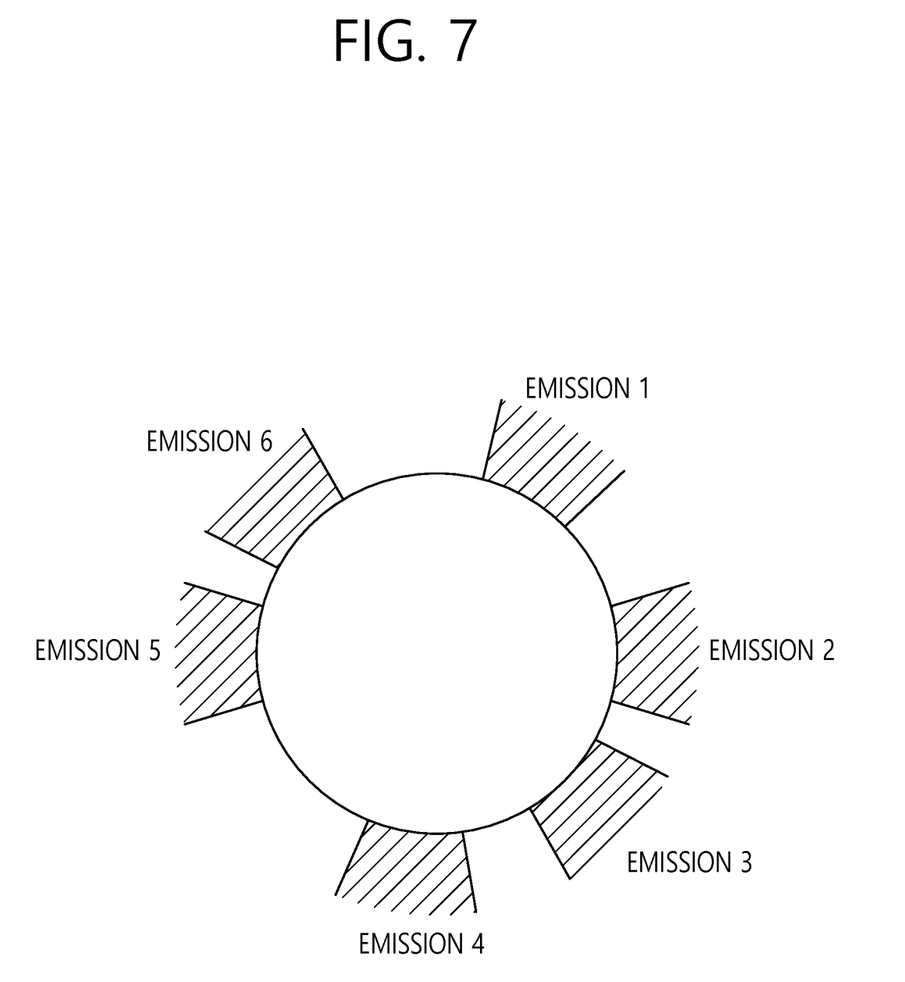

In addition, according to the present invention, the radiation direction may be adjusted continuously. That is, depending on a degree of rotation, the position of the radiation source may be changed, not in phases, but continuously. Thus, radiation may be emitted in a desired direction, as shown in FIG. 7.

Figure 8:
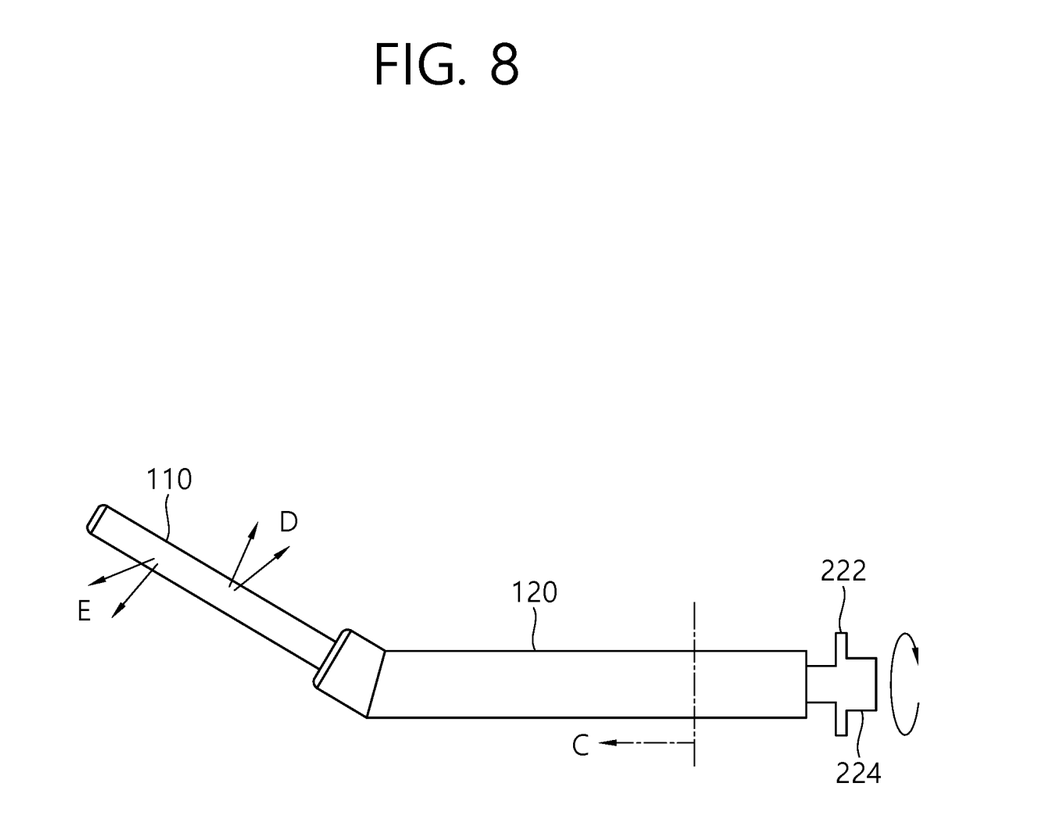
FIGS. 8 and 9 are for explanation of cancer treatment using an insertable device according to the present invention.
Figure 9:
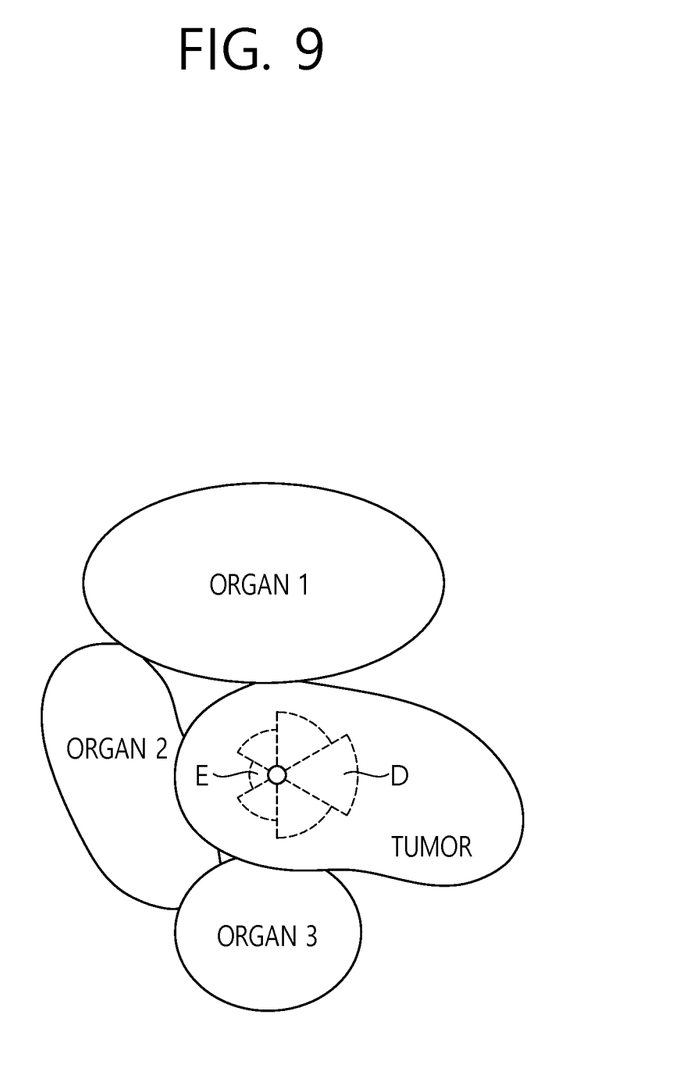

With reference to FIGS. 8 and 9, treatment of uterine cancer using the insertable device according to the present invention will be described.

The insertable device 1 is inserted into a human body and then the radiation source is introduced into the insertable device 1. When the insertion is completed, the right side at a position "C" in FIG. 8 is exposed to an outside of the human body. In addition, the first outer body 110 is inserted into a position of a tumor in accordance with a bent structure of the insertable device 1 inside the human body. In another embodiment, after the radiation source is introduced into the insertable device 1, the insertable device 1 may be inserted into the human body.

In this state, based on a shape and a position of a tumor found in a previous medical examination, the medical profession adjusts a position and a radiation direction of the radiation source according to a lengthwise direction of the first outer body 110. The radiation direction of the radiation source is adjusted by adjusting the operator, as described above.

When the position of the radiation source is determined with respect to a tumor shape as shown in FIG. 9, emission time is increased in a direction toward D where many tumors exist, so that sufficient radiation is emitted. On the other hand, emission time is reduced in a direction toward E where few tumors exist, so that emission of radiation toward surrounding organs is minimized.

During this treatment process, a radiation emission direction may be easily adjusted using the insertable device 1 of the present invention, and the radiation source may be easily inserted and removed.

In the above description, treatment of uterine cancer is exemplified, but the insertable device of the present invention is not limited thereto and is applicable even to head and neck cancer, esophageal cancer, rectal cancer, and the like.

Figure 10:
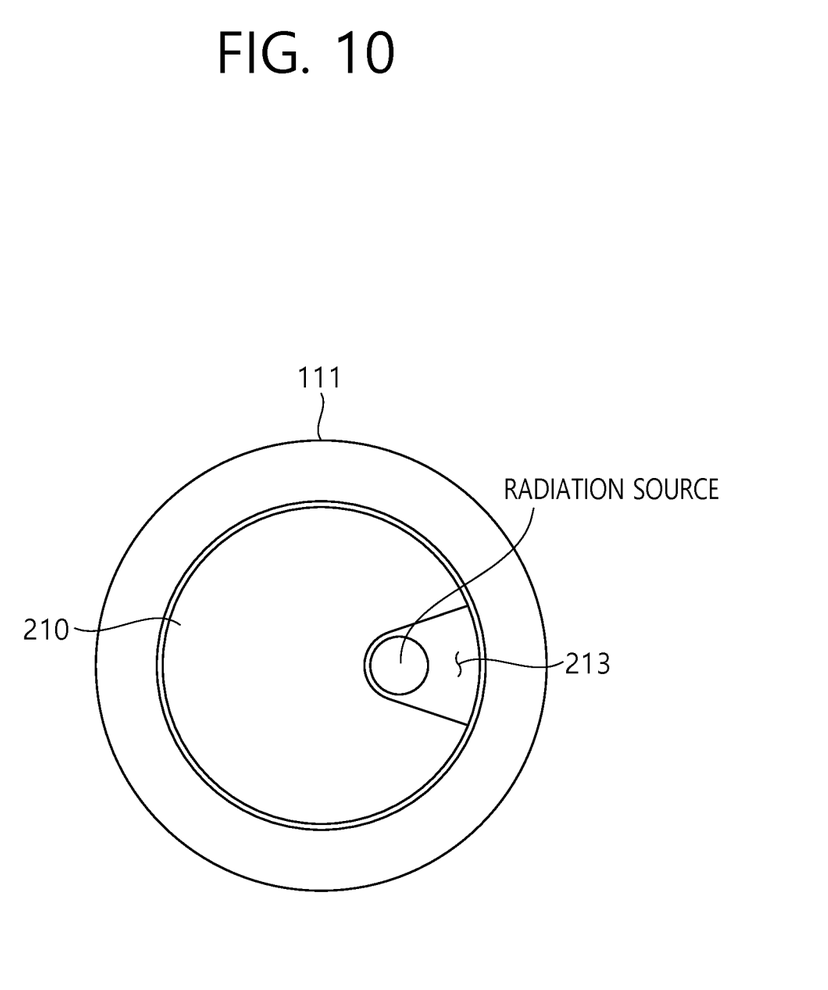
FIG. 10 illustrates an exemplary variation of an insertable device according to the present invention.

FIG. 10 illustrates a variation of an insertable device according to the present invention.

In an exemplary variation, the accommodation space 213 is formed to be widen in proportion to distance from the radiation source. Formation of the accommodation space 213 may be changed in various ways. Alternatively, the accommodation space 213 may be formed such that the radiation source is positioned at the center of the first inner body 210.

In another variation, an insertion angle, that is, an angle between the first outer body 110 and the second outer body 120, may be adjusted. The insertion angle may be adjusted and fixed outside a human body. Angle adjustment may be performed continuously or in stepwise, and a well-known configuration may be adapted for angle adjustment configuration.

In yet another variation, the inner connection part 230 is integrally formed with at least one of the first inner body 210 or the second inner body 220.

The above embodiments are illustrative purpose only for the present invention and an exemplary embodiment of the present invention not limited thereto. Since numerous variations and modifications will become apparent to those skilled in the art once the above disclosure is fully appreciated, the scope and spirit of the invention come within the scope of the appended claims and their equivalents.

The invention claimed is:

1. An insertable brachytherapy device for adjusting radiation emission direction comprising:
    an outer body including a first outer body, a second outer body, and a bent part for connecting the first outer body and the second outer body such that the outer body is bent;
    an inner body including a first inner body, a second inner body, and an inner connection part comprising a rotation power mechanism, the inner connection part connecting the first inner body and the second inner body;
    wherein the first inner body is positioned inside the first outer body and includes an accommodation space in which a radiation source is accommodated, the second inner body is positioned inside the second outer body and includes a guide space enabling the radiation source to pass therethrough, the second inner body being capable of rotating, and the inner connection part is positioned in correspondence to the bent part of the outer body, the inner connection part having a connection space communicating with the guide space and the accommodation space such that the radiation source is allowed to pass through the connection space and the guide space, and
    wherein the first inner body is separated from the first outer body and rotated by the rotation of the second inner body.

2. The insertable brachytherapy device of claim 1, wherein the accommodation space extends along the first inner body.

3. The insertable brachytherapy device of claim 2, wherein the accommodation space comprises a trench formed within the first inner body.

4. The insertable brachytherapy device of claim 3, further comprising a position limiting part positioned within the accommodation space adjacent the first outer body and limiting a position of the radiation source.

5. The insertable brachytherapy device of claim 2,
wherein the first inner body has a circular vertical cross-sectional shape, and
wherein the accommodation space accommodates the radiation source at an eccentric position with respect to a longitudinal axis of the accommodation space.

6. The insertable brachytherapy device of claim 2,
wherein the accommodation space comprises:
a first accommodation space; and
a second accommodation space positioned between the first accommodation space and the connection space, and
wherein the second accommodation space has a cross-sectional area greater than a cross-sectional area of the first accommodation space.

7. The insertable brachytherapy device of claim 6, wherein the cross-sectional area of the second accommodation space increases in proportion to proximity to the connection space.

8. The insertable brachytherapy device of claim 2,
wherein the guide space comprises:
a first guide space; and
a second guide space positioned between the first guide space and the connection space, and
wherein the second guide space has a cross-sectional area greater than a cross-sectional area of the first guide space.

9. The insertable brachytherapy device of claim 8, wherein the cross-sectional area of the second guide space increases in proportion to proximity to the connection space.

10. The insertable brachytherapy device of claim 2, wherein the first inner body is made of a material with radiation shielding.

11. The insertable brachytherapy device of claim 2, wherein an angle of emission of radiation from the radiation source to an outside of the first outer body is 5 degrees to 180 degrees.

12. The insertable brachytherapy device of claim 1, wherein the rotation power mechanism comprises at least one of a flexible shaft, a bellows, or a joint.

13. The insertable brachytherapy device of claim 12, wherein one end of the inner connection part is fixed to the first inner body, and the other end of the inner connection part is connected to the second inner body.

14. The insertable brachytherapy device of claim 12, wherein the inner connection part and the outer body are spaced from each other such that the inner connection part rotates in correspondence to the outer body when the inner connection part is transformed in response to rotation of the second inner part.

* * * * *